United States Patent

Lev

[11] Patent Number: 5,951,566
[45] Date of Patent: *Sep. 14, 1999

[54] ANNULAR CATHETER

[76] Inventor: Shlomo Lev, 25 Ahronowitz Street, Holon, Israel

[ * ] Notice: This patent is subject to a terminal disclaimer.

[21] Appl. No.: 08/808,935

[22] Filed: Feb. 28, 1997

Related U.S. Application Data

[63] Continuation-in-part of application No. 08/778,329, Jan. 2, 1997, Pat. No. 5,851,218.

[51] Int. Cl.⁶ ...................................................... A61F 11/00
[52] U.S. Cl. .............................. 606/108; 606/198; 623/1; 623/12
[58] Field of Search ...................................... 604/104, 164, 604/264; 606/1, 108, 191–200; 600/201, 204, 207; 623/1, 11, 12

[56] References Cited

U.S. PATENT DOCUMENTS

| | | |
|---|---|---|
| 3,794,041 | 2/1974 | Frei et al. . |
| 4,063,561 | 12/1977 | McKenna . |
| 4,161,943 | 7/1979 | Nogler . |
| 4,244,362 | 1/1981 | Anderson . |
| 4,593,687 | 6/1986 | Gray et al. . |
| 5,041,092 | 8/1991 | Barwick . |
| 5,089,006 | 2/1992 | Stiles . |
| 5,176,618 | 1/1993 | Freedman . |
| 5,195,984 | 3/1993 | Schatz . |
| 5,269,759 | 12/1993 | Hernandez et al. . |
| 5,271,743 | 12/1993 | Hattler . |
| 5,370,691 | 12/1994 | Samson . |
| 5,378,239 | 1/1995 | Termin et al. . |
| 5,431,640 | 7/1995 | Gabriel . |
| 5,496,277 | 3/1996 | Termin et al. . |
| 5,507,770 | 4/1996 | Turk ......................................... 606/198 |
| 5,549,555 | 8/1996 | Sohn . |

FOREIGN PATENT DOCUMENTS

WO 96/21488    1/1996    WIPO .

*Primary Examiner*—Glenn K. Dawson
*Attorney, Agent, or Firm*—Mark M. Friedman

[57] ABSTRACT

A catheter, including: (a) an element; (b) an adjustable ring attached to the element such that at least a portion of the element is substantially within the adjustable ring, the adjustable ring having at least a first diameter and at least a second diameter, and the adjustable ring being magnetizable; and (c) a magnetization unit located near a portion of the element, the magnetization unit determining when the adjustable ring has the first diameter and when the adjustable ring has the second diameter.

12 Claims, 11 Drawing Sheets

ANNULAR CATHETER

This Application is a Continuation-in-Part of U.S. application Ser. No. 08/778,329, filed on Jan. 2, 1997, now U.S. Pat. No. 5,851,218.

FIELD AND BACKGROUND OF THE INVENTION

The present invention relates to a catheter intended to dilate biological ducts, such as occluded and narrowed blood vessels and, more particularly, to a catheter made of an elastic ring whose diameter and force of exertion is controlled by the application of a magnetic field. The elastic ring is able to expand while permitting substantially unchanged flow of fluid, such as blood through the catheter.

Cardiovascular disease is a growing problem in many countries. One of the hallmarks of this disease is the narrowing or occlusion of blood vessels, such as arteries and veins, by the deposition of fats and cholesterol on the walls of these vessels. Balloon catheters are well known in the art for broadening such narrowed or occluded blood vessels. Several types of such balloon catheters are known, all of which have a balloon located at one end of an elastomeric tubule and all of which operate by the same general principles. First, the catheter with the empty, flexible balloon is inserted into the narrowed or occluded blood vessel by using a wire guide. Next, the balloon, which can be ellipsoidal or spherical, is inflated and made rigid as a result of application of water pressure within the catheter. As the balloon is made rigid, it forcibly dilates the narrowed or occluded blood vessel, fractures the deposits of fats or cholesterol on the vessel walls and pushes them aside. This dilation stretches, and often tears, the tissues' fibers in the wall of the blood vessel. With the release of internal pressure within the balloon, it returns to its original diameter while the vessel walls remain laterally displaced and open to blood flow. The catheter, and the balloon at its end, are then removed from the blood vessel.

One important safety factor is the rate of dilation of the blood vessel. A slower rate of dilation is much safer since the tissues' fibers are less likely to tear, and complications, such as a rupture of the blood vessel, are less likely to occur. Thus, a slow rate of dilation is strongly preferable.

Unfortunately, all of these balloon catheters have one major drawback: they substantially block the flow of blood through the blood vessel when the balloon is inflated and made rigid. Such a blockage deprives those tissues supplied by the blood vessel of blood, and hence of oxygen and nutrients, during the period when the balloon is inflated. This deprivation is particularly dangerous for sensitive tissues, which cannot tolerate an interruption in blood supply. Furthermore, such an interruption often causes significant patient discomfort which can even "feel like a heart attack".

In an attempt to solve this problem, a perfusion balloon catheter has been developed for use with blood vessels supplying sensitive tissues. This catheter has openings in the catheter wall before and after the balloon, connected by small tubes passing through the balloon internally, so that blood can perfuse through the catheter. Unfortunately, these openings only permit a small fraction of the blood to flow through the catheter, so that the blood flow is slow and significant patient discomfort is still present. Thus, even using such a perfusion balloon, the catheterization must be done extremely rapidly to avoid damage to sensitive tissues. Furthermore, extremely sensitive tissues, such as the brain, cannot even tolerate such a significant reduction in blood flow, so that blood vessels directly supplying the brain cannot be catheterized. Thus, the perfusion catheter does not adequately solve the problems of balloon catheters, such as the need for rapid dilation of the blood vessel.

However, as noted above, rapid dilation of the blood vessel is undesirable. Such rapid dilation can potentially lead to serious complications, such as rupture of the blood vessel, yet paradoxically, these serious complications must be risked during catheterization to avoid prolonged low blood flow through the vessel.

There is thus a widely recognized need for, and it would be highly advantageous to have, a catheter which can forcibly dilate an occluded or narrowed blood vessel without a substantial reduction in blood flow through the vessel, so that dilation can occur relatively slowly even when the blood vessel is supplying a highly sensitive organ, such as the brain.

SUMMARY OF THE INVENTION

According to the present invention, there is provided a catheter, including: (a) an element for transferring a magnetic force; (b) an adjustable ring attached to the element such that at least a portion of the element is substantially within the adjustable ring, the adjustable ring having at least a first diameter and at least a second diameter, and the adjustable ring being magnetizable; and (c) a magnetization unit located near a portion of the element, the magnetization unit regulating the magnetic force transferred by the element for determining when the adjustable ring has the first diameter and when the adjustable ring has the second diameter. Preferably, the element is a rod formed of magnetizable metal, and the magnetization unit includes an induction coil wrapped substantially around at least a portion of the rod, such that when current is passed through the induction coil in one direction, the rod transfers the magnetic force with one direction of polarity, and when the current is passed through the induction coil in an opposing direction, the rod transfers the magnetic force with opposing polarity. Alternatively and preferably, the element is a rod formed of magnetizable metal, and the magnetization unit includes a permanent magnet, a distance of the magnet from the rod determining the magnetic force. Also preferably, the adjustable ring is magnetizable by a magnetic unit and the form of the magnetic unit is selected from the group consisting of powder, foil and chip.

According to another embodiment of the present invention, there is provided a method of catheterizing a biological duct of a subject, including the steps of: (a) inserting the catheter of claim 1 into the biological duct of the subject with the adjustable ring of the catheter having the first diameter such that the adjustable ring substantially does not contact the wall of the biological duct; (b) regulating the magnetic force transferred by the element such that the adjustable ring has the second diameter, the second diameter being substantially larger than the first diameter; and (c) contacting the wall of the biological duct with the adjustable ring having the second diameter. Preferably, the wall of the biological duct is contacted more than once.

According to yet another embodiment of the present invention, there is provided a method of assembling a catheter, including the steps of: (a) preparing an adjustable ring from flexible and magnetizable material; (b) attaching the adjustable ring to an element for transferring a magnetic force; and (c) placing a magnetization unit near the element, such that the magnetization unit transmits the magnetic force. Preferably, the element is a rod and the magnetization unit is formed by wrapping an induction coil substantially around at least a portion of the rod. Alternatively and preferably, the magnetization unit is formed from a permanent magnet.

According to still another embodiment of the present invention, there is provided a repair catheter for repairing a wall of a biological duct, including: (a) an element for transferring a magnetic force; (b) a stent, at least a portion of the element being substantially within the stent, the stent having at least a first diameter and at least a second diameter, the stent being magnetizable and the stent containing activatable adhesive; and (c) a magnetization unit located near a portion of the element, the magnetization unit regulating the magnetic force transferred by the element for determining when the stent has the first diameter and when the stent has the second diameter, the activatable adhesive being activated when the stent has the second diameter such that the stent becomes substantially rigid.

According to still another embodiment of the present invention, there is provided a suction catheter for removing a deposit from a biological duct, the biological duct having a wall, the suction catheter including: (a) a rod for transferring a magnetic force, the rod being substantially hollow; (b) an adjustable ring attached to the rod such that at least a portion of the rod is substantially within the adjustable ring, the adjustable ring having at least a first diameter and at least a second diameter, and the adjustable ring being magnetizable; (c) a magnetization unit located near a portion of the rod, the magnetization unit regulating the magnetic force transferred by the rod for determining when the adjustable ring has the first diameter and when the adjustable ring has the second diameter, such that when the adjustable ring has the second diameter, the adjustable ring contacts the wall of the biological duct; and (d) a suction device attached to a portion of the rod, the suction device exerting a vacuum force to remove the deposit from the biological duct when the adjustable ring contacts the wall of the biological duct.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a catheter which can be used to forcibly dilate, and therefore clear, narrowed or occluded blood vessels. Specifically, the catheter includes an adjustable ring whose diameter is controlled by the application of a magnetic field. The adjustable ring is able to expand while permitting substantially unchanged flow of blood through the catheter. Preferably, the catheter is also used to apply a stent to a blood vessel wall to effect a repair of that wall. Also preferably, the catheter includes a suction pump to remove deposits on the walls of the occluded or narrowed blood vessel.

Although both the aforementioned and the following descriptions specifically describe a catheter for use with blood vessels, it should be understood that this is for clarity only and that the catheter can be inserted into any biological duct including, but not limited to, the gastrointestinal tract, urological ducts, gall bladder and passages of the lung.

It should be noted in passing that U.S. Pat. No. 5,089,006 to Stiles (hereinafter referred to as "Stiles") describes a biological duct liner and installation catheter which can use a magnetic field during the installation of the liner. However, the catheter disclosed by Stiles differs from that of the present invention in a number of ways. First, the catheter of Stiles is intended only for the installation of the liner, while the catheter of the present invention can also be used to forcibly dilate a biological duct and can then be removed. Second, the adjustable ring of the present invention can be expanded and contracted to a variable diameter, while the liner of Stiles is only intended to expand to a predetermined diameter. Finally, the stent of the present invention includes an activatable adhesive, while the liner of Stiles does not.

The principles and operation of a catheter according to the present invention may be better understood with reference to the drawings and the accompanying description.

Figure 1:
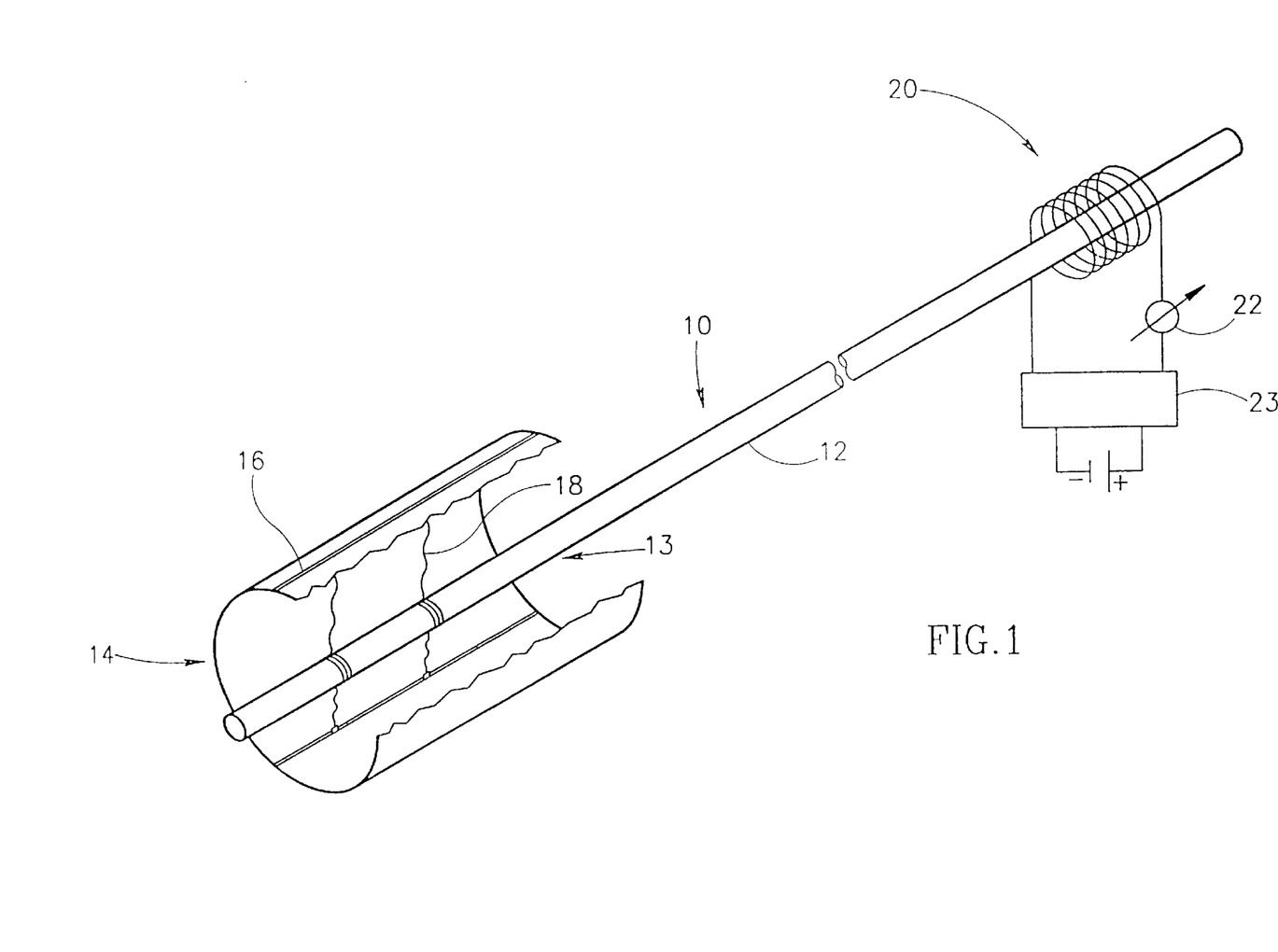
FIG. 1 is a view of one embodiment of the present invention.

Referring now to the drawings, FIG. 1 illustrates a catheter according to the present invention. Catheter 10 has an element 12 for transferring a magnetic force, preferably in the form of a rod and preferably made of magnetizable metal, most preferably of soft metal. Hereinafter, the term "magnetizable" is defined as either permanently or temporarily capable of transferring a magnetic force. Element 12 also preferably includes an annulus attached to element 12, through which a wire guide can be threaded (not shown). At one portion 13 of element 12, there is an adjustable ring 14, shown partially cut-away in FIG. 1 (see also FIG. 2A below for a complete view). Hereinafter, the term "ring" includes both an annular ring and a cross-section of a cylinder. The ring can have one of three alternative forms. First, the ring can be a coil, preferably formed from a single, helically wound strip or wire. Second, alternatively and preferably, the ring can be an open weave net. Third, alternatively and most preferably, the ring is substantially continuous, such that the ring is a single piece of material without a beginning or an end. Adjustable ring 14 is magnetizable. Adjustable ring 14 preferably has at least one, and most preferably a plurality of, supporting ribs 16 attached to adjustable ring 14. Ribs 16 act to stiffen adjustable ring 14. Adjustable ring 14 is attached to element 12, preferably by at least one, and most preferably a plurality of, fibers 18. Hereinafter, "attached" is defined as connected to, or integrally formed with. Fibers 18 are preferably made from a strong, synthetic material such as polyamide.

At another portion of element 12, there is an induction coil 20. Induction coil 20 is wrapped substantially around element 12 and is then preferably attached to a rheostat 22. Rheostat 22 regulates the flow of electricity from a source of electricity (not shown) through induction coil 20. A switch 23 is preferably used to determine the direction of the flow of electricity. When electricity is permitted to flow through induction coil 20, element 12 becomes magnetized. The polarity of element 12 depends upon the direction of the flow of electricity through induction coil 20. Induction coil 20, preferably together with rheostat 22, forms a magnetization unit for regulating the magnetic force transferred by element 12. Most preferably, electricity flowing through induction coil 20 is alternating current, so that the direction of flow is changeable, although direct current can be alternatively used.

Figure 2A:
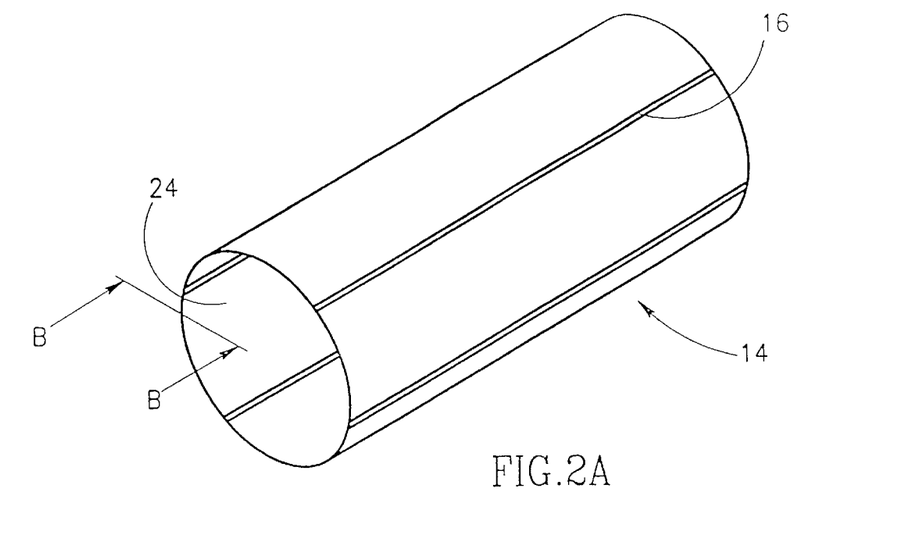
FIGS. 2A and 2B are views of an adjustable ring according to the present invention.
Figure 2B:
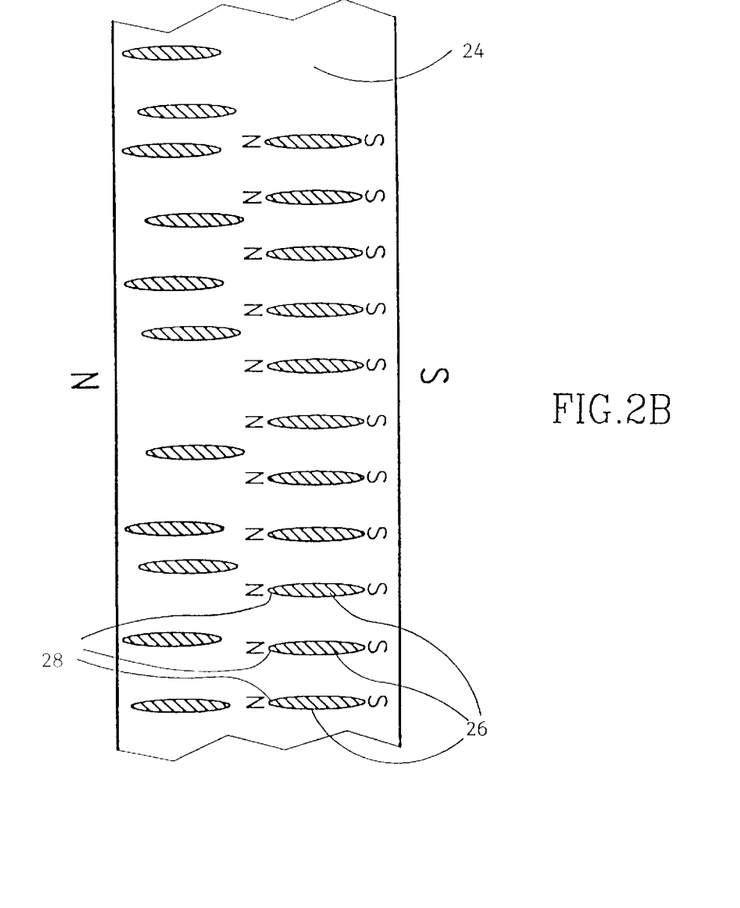

FIGS. 2A and 2B are views of adjustable ring 14. FIG. 2A shows a perspective view of adjustable ring 14. Ribs 16 can also be seen disposed around adjustable ring 14. FIG. 2B shows a cross-section of adjustable ring 14 through line B—B. A cross-section of a portion of a wall 24 of adjustable ring 14 can be seen. Adjustable ring 14 is preferably magnetizable as follows. Attached to wall 24, and preferably embedded in wall 24, is at least one, and preferably a plurality of, magnetic units 26. If there is more than one magnetic unit 26, at least a portion of said magnetic units 26 is arranged with the same pole 28 facing inward towards the interior of adjustable ring 14. Pole 28 has fixed polarity, which can be either north or south. However, the polarity of portion 13 of element 12 alternates. Thus, depending upon the direction of the current through induction coil 20, pole 28 alternately has the identical or the opposite polarity of portion 13 of element 12. Each magnetic unit 26 can be any form of material, such as magnetizable metal, which causes adjustable ring 14 to be magnetizable including, but not limited to, powder either coated on wall 24 or embedded within wall 24, or both, a chip or a thin section of foil either attached to wall 24 or embedded within wall 24, or both. If powder is used, preferably each magnetic unit 26 is arranged vertically in relation to element 12.

The present invention can be operated in the following manner. Catheter 10 is inserted into a blood vessel of a subject via a standard catheter lead (not shown). Hereinafter, the term "subject" refers to a human or lower animal into whom catheter 10 is inserted. During this part of the procedure, the current does not flow through induction coil 20, or alternatively passes through induction coil 20 in a direction which causes portion 13 of element 12 to have the opposite polarity as pole 28 of each magnetic unit 26. Portion 13 thus attracts pole 28. It should be noted that although element 12 is not magnetized by induction coil 20 when the current through induction coil 20 is substantially zero (i.e.—does not flow), since element 12 is made from magnetizable metal, element 12, or more specifically portion 13 of element 12, still attracts pole 28. At this point, adjustable ring 14 is collapsed (not shown) and therefore has a sufficiently small first diameter to permit the insertion of adjustable ring 14 into the blood vessel substantially without adjustable ring 14 contacting the walls of the blood vessel. It should be noted that in this embodiment, induction coil 20 remains substantially outside the subject's body (not shown).

When catheter 10, and more specifically adjustable ring 14, is located at the section of blood vessel to be dilated, rheostat 22 permits the flow of electricity through induction coil 20 in a direction which causes element 12 to become magnetized with opposite polarity to the previous polarity of element 12, or alternatively permits electricity to start to flow through induction coil 20, so that pole 28 of each magnetic unit 26 has the identical polarity as portion 13 of element 12. Now each magnetic unit 26, and hence wall 24, is repelled away from element 12. Adjustable ring 14 now expands to have a second, larger diameter, forcing the blood vessel to dilate (not shown). The rate of the expansion of adjustable ring 14, and hence of the dilation of the blood vessel, is controlled by the flow of electricity through induction coil 20. Such flow also controls the extent of the expansion of adjustable ring 14, since increasing the current also increases the repulsion between each magnetic unit 26 and element 12. Such an increase in repulsion increases the diameter of adjustable ring 14.

The maximum diameter of adjustable ring 14 is preferably at least partly determined by the length of fibers 18, which attach adjustable ring 14 to element 12. Fibers 18 act to maintain the position of adjustable ring 14 relative to element 12.

During the dilation of adjustable ring 14, it should be noted that the flow of blood through the blood vessel is substantially unaltered by catheter 10. This is because adjustable ring 14 is substantially hollow, so that only element 12 presents any obstruction to the flow of blood. Thus, the supply of blood, and hence of oxygen and nutrients, to tissue fed by the blood vessel is substantially unimpaired. Furthermore, since the flow of blood is substantially unimpaired, the rate of dilation of the blood vessel can be relatively slow, enabling the fibers of the walls of the vessel to be slowly stretched, rather than torn as with a balloon catheter.

After the blood vessel has been dilated, the flow of current through induction coil 20 is again either reversed or stopped by rheostat 22. Portion 13 of element 12 now has the opposite polarity as pole 28 of each magnetic unit 26. Portion 13 thus attracts pole 28. Wall 24 of adjustable ring 14 is now attracted towards element 12, causing adjustable ring 14 to collapse back to the first diameter. Catheter 10 may now be safely withdrawn from the subject's body. It should be noted that adjustable ring 14 is preferably able to have a number of different diameters, rather than just the two diameters described herein for purposes of illustration.

As noted above, adjustable ring 14 preferably has at least one, and preferably a plurality of, supporting ribs 16 attached to adjustable ring 14. Ribs 16 prevent buckling of adjustable ring 14, or of its edges, when the current through induction coil 20 is such that wall 24 is attracted toward element 12. Ribs 16 are preferably formed of material which is not affected by the magnetic field, so that the expansion of adjustable ring 14 is not altered.

Catheter 10, as illustrated in FIGS. 1, 2A and 2B, can be assembled as follows. First, induction coil 20 is wrapped substantially around element 12. Induction coil 20 is then preferably connected to rheostat 22, which is eventually connected to a source of electricity (not shown). Rheostat 22 does not need to be connected to the source of electricity until catheter 10 is to be operated.

Next, adjustable ring 14 is made from flexible and magnetizable material, preferably by attaching, and most preferably embedding, at least one, and preferably a plurality of, magnetic units 26 in flexible material. Poles 28 of magnetic units 26 should be oriented as described above, so that at least a portion of magnetic units 26 have the same pole 28 facing toward the interior of adjustable ring 14, if there is more than one magnetic unit 26. Preferably, at least one, and preferably a plurality of, supporting ribs 16 are then attached to adjustable ring 14. Finally, adjustable ring 14 is attached to portion 13 of element 12, preferably by at least one, and most preferably a plurality of, fibers 18.

Figure 3:
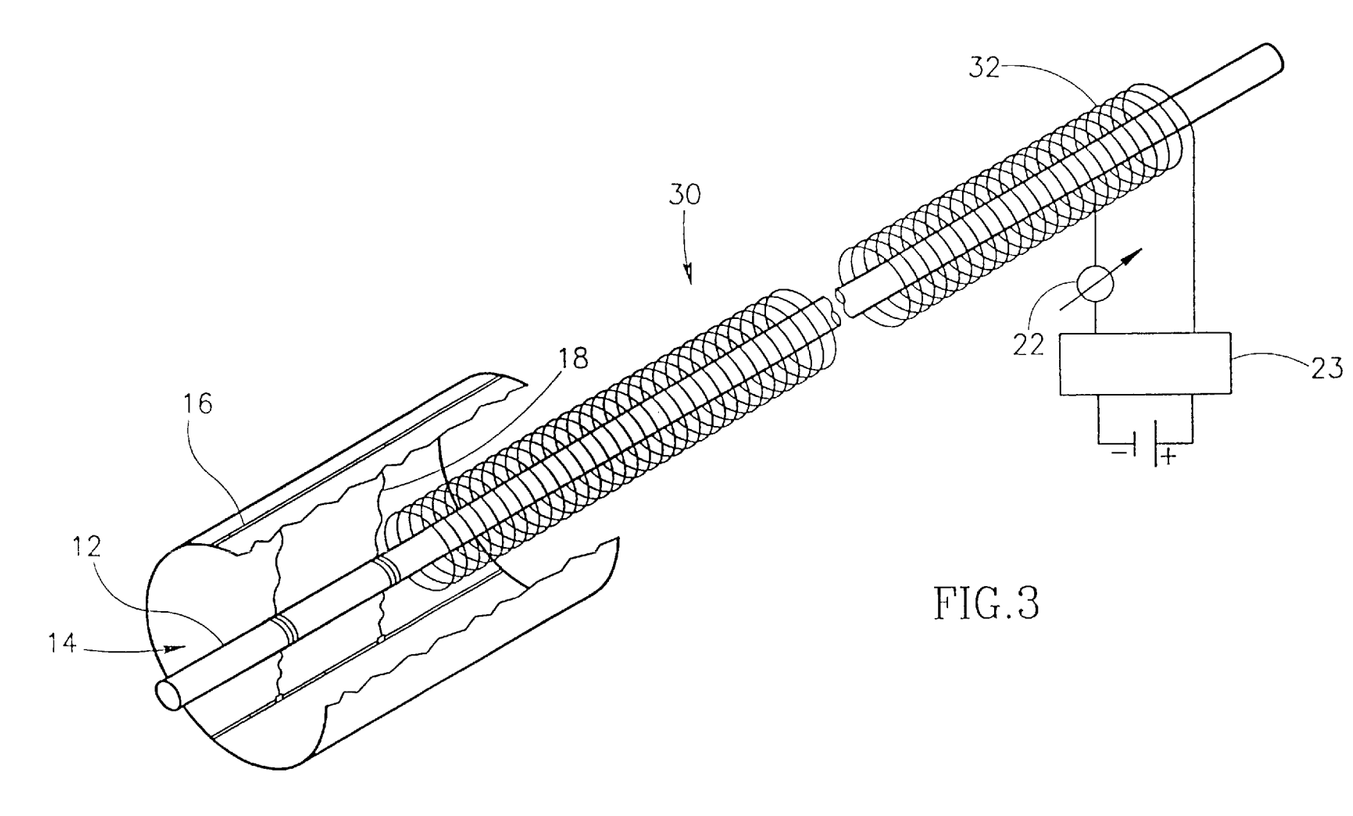
FIG. 3 is a view of a second embodiment of the present invention, in which the induction coil is extended along substantially a majority of the element.

FIG. 3 is a view of a second embodiment of the present invention. In this embodiment, a catheter 30 is very similar to catheter 10 of FIG. 1, with one exception. An induction coil 32 of catheter 30 extends along substantially a majority of element 12 and makes a loop. Also, induction coil 32 preferably extends substantially inside the body of the subject during normal operation. Preferably, induction coil 32 extends from one portion of element 12 substantially near adjustable ring 14, and most preferably extends within adjustable ring 14. Catheter 30 has a substantially similar mode of operation as catheter 10 of FIG. 1. Catheter 30 is also similarly assembled, except that induction coil 32 is placed on element 12 so as to extend along substantially a majority of element 12 and then to return along element 12, preferably extending inside the body of the subject during normal operation.

Figure 4:
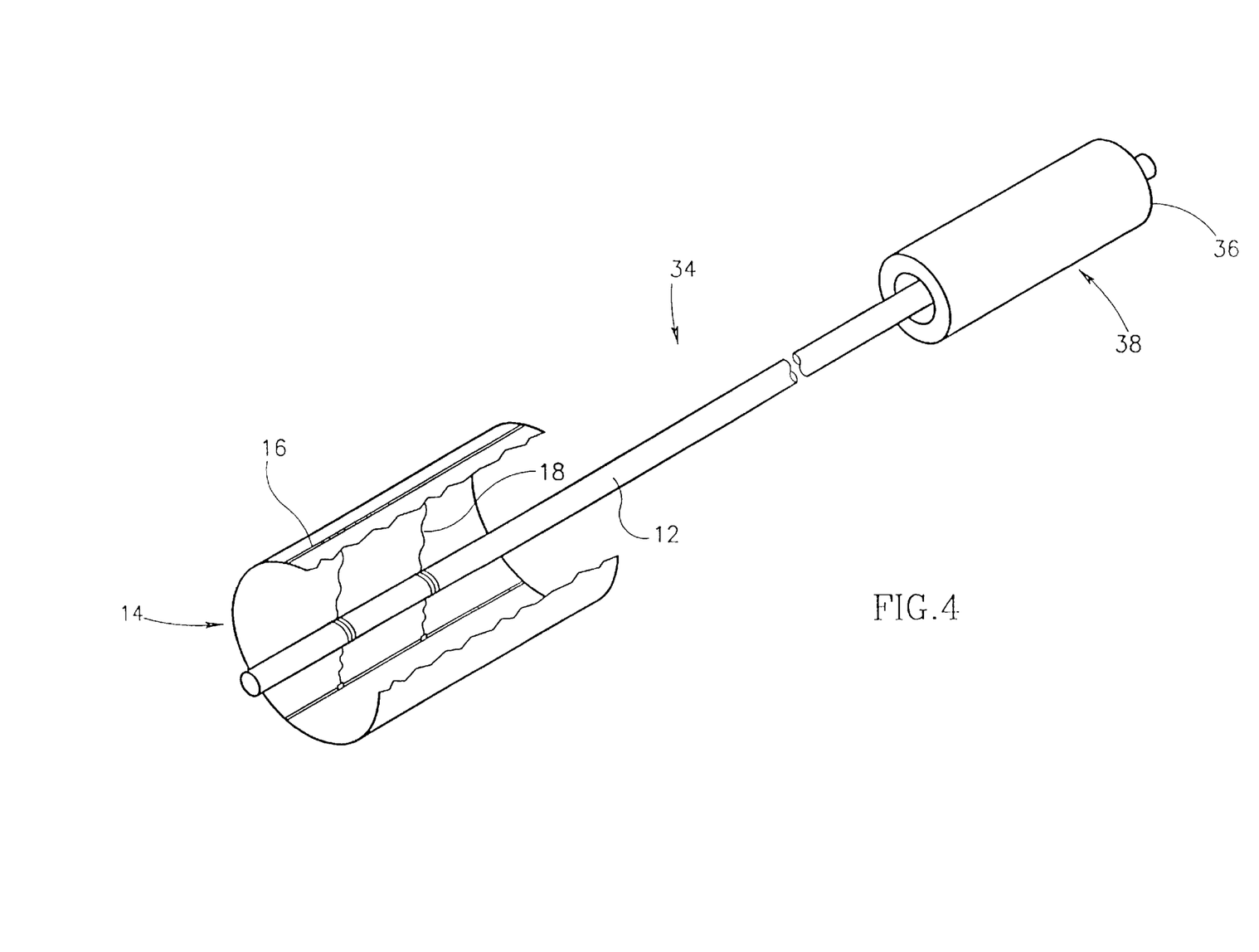
FIG. 4 is a view of a third embodiment of the present invention, in which the induction coil is replaced by a substantially permanent magnet.

FIG. 4 is a view of a third embodiment of the present invention, in which the induction coil is replaced by a substantially permanent magnet. In this embodiment, a catheter 34 is again substantially similar to catheter 10 of FIG. 1, with one exception. Catheter 34 does not have an induction coil. Instead, a permanent magnet 36 is located at one portion of element 12. A sleeve 38 preferably then extends from permanent magnet 36 along element 12. The degree of expansion, and hence the diameter, of adjustable ring 14 is controlled by the strength of permanent magnet 36. At least permanent magnet 36, and preferably permanent magnet 36 and sleeve 38, form a magnetization unit for catheter 34. The magnetization of element 12 is controlled by the placement of the magnetization unit relative to element 12, such that when the magnetization unit is near element 12, element 12 is magnetized; and when the magnetization unit is not near element 12, element 12 is not magnetized.

Catheter 34 is assembled in a substantially similar manner as catheter 10, except that no induction coil 20 is wrapped around element 12 and no rheostat 22 is used. Instead, sleeve 38 is attached to permanent magnet 36. Sleeve 38 is then slipped over element 12, so that element 12 is substantially inside sleeve 38.

Figure 5:
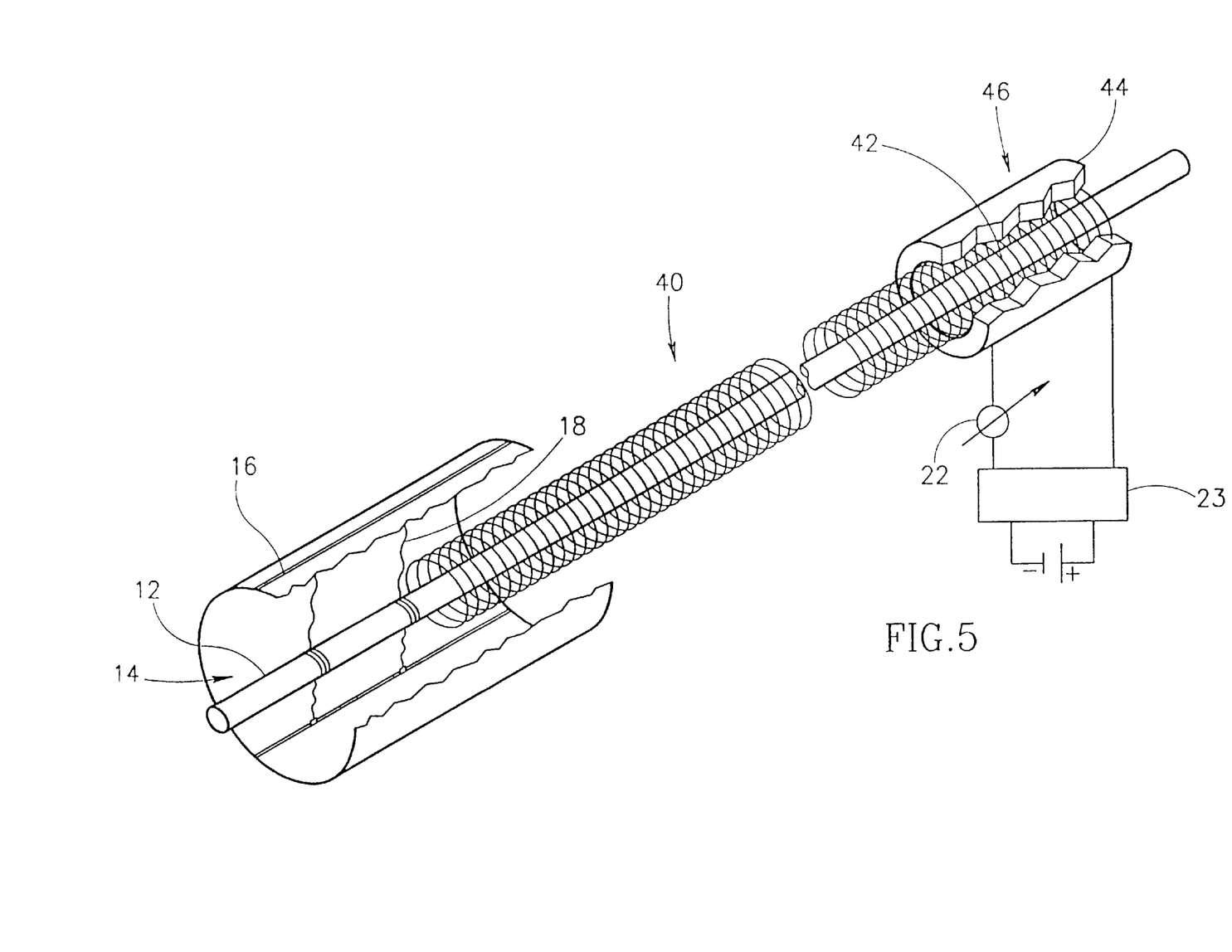
FIG. 5 is a view of a fourth embodiment of the present invention, in which features of embodiments illustrated in FIGS. 1 or 3 and 4 are combined.

FIG. 5 is a view of a fourth embodiment of the present invention, in which features of embodiments illustrated in FIGS. 1 or 3 and 4 are combined. A catheter 40 has both an induction coil 42, like catheter 10 of FIG. 1 or alternatively like catheter 30 of FIG. 3, depending upon the length of induction coil 42, and a permanent magnet 44 shown partially cut-away, like catheter 34 of FIG. 4. A sleeve 46 extends from permanent magnet 44 along element 12. When current flows through induction coil 42 in one direction, the magnetization of element 12 in the polarity of permanent magnet 44 is augmented and adjustable ring 14 expands. When current either flows through induction coil 42 in the opposite direction or does not flow, the magnetization of element 12 has the opposite polarity of permanent magnet 44 and adjustable ring 14 collapses (not shown).

In this case, at least permanent magnet 44 and induction coil 42, and preferably permanent magnet 44 and sleeve 46, and induction coil 42 and rheostat 22, form a magnetization unit for catheter 34.

Catheter 40 is assembled in a substantially similar manner as catheters 10 and 34. Catheter 40 is assembled as for catheter 10. Next, sleeve 46 is attached to permanent magnet 44. Sleeve 46 is then slipped over element 12, so that element 12 is substantially inside sleeve 46.

Preferably, element 12 in any of the embodiments of FIGS. 1–6 is hollow. Also preferably, element 12 and adjustable ring 14 are both coated with a material which rejects adhesion by blood, cholesterol or other tissue components. Most preferably, the material is polytetrafluoroethylene. Alternatively and preferably, rather than being made from magnetizable metal, element 12 is made from material which is permanently magnetic. In this case, the magnetization of element 12 will be neutralized by induction coil 20 or 42, depending on which embodiment is desired.

Figure 6:
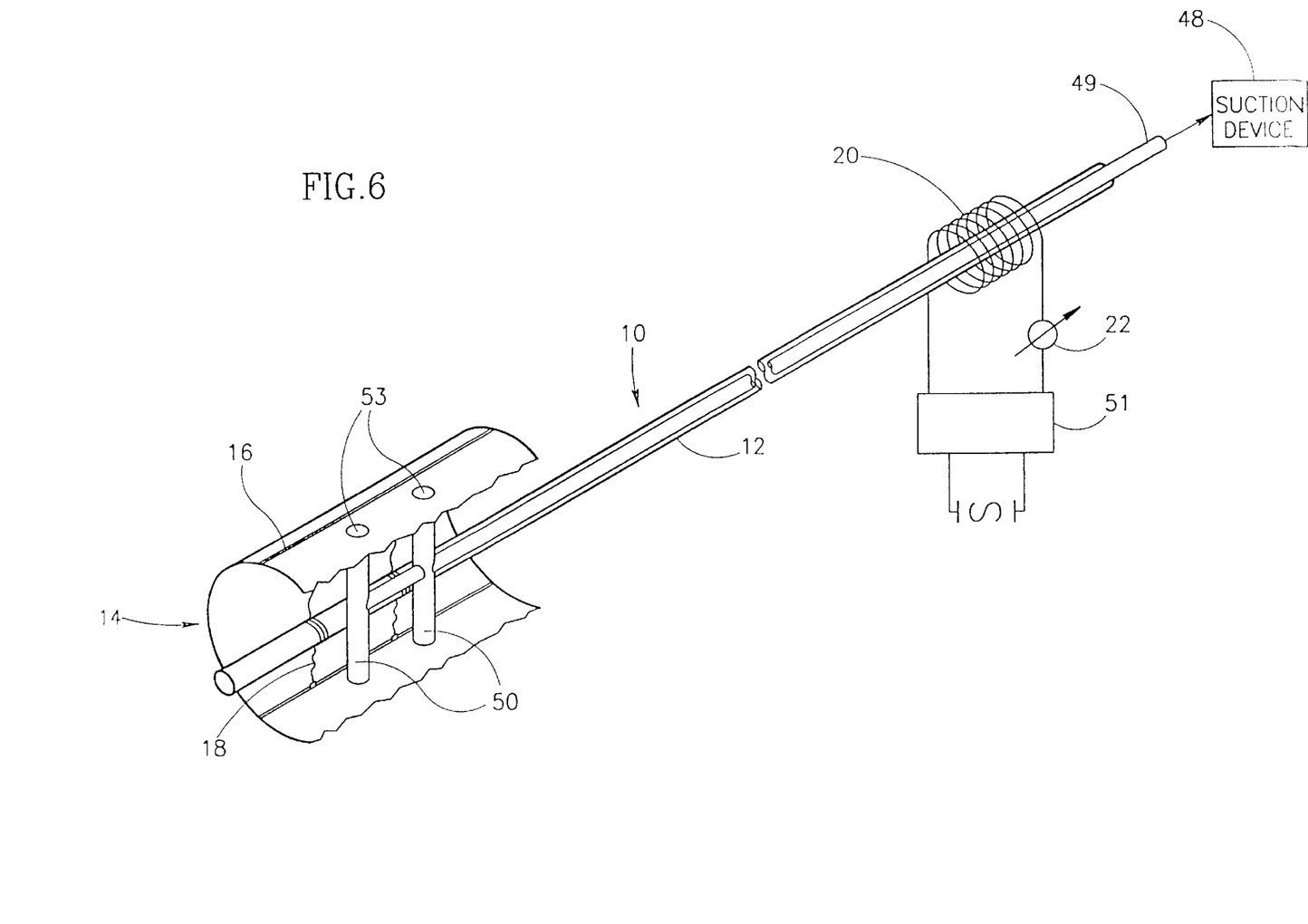
FIG. 6 is a view of a catheter and suction device according to the present invention.

FIG. 6 is a view of a catheter with a suction device according to the present invention. Catheter 10 is shown with a suction device 48, which can be a pump, for example. Element 12 is preferably hollow in this embodiment, although element 12 can alternatively be substantially solid and an extra hollow tube 49 present as shown. In the first case, element 12 alone is a suction element, while in the second case, element 12 and tube 49 together form the suction element. The suction element also preferably includes at least one, and preferably a plurality of, suction tubes 50 connected to the suction element. The opening of each suction tube 50 should be placed at or near a least one, and preferably a plurality of openings 53 in adjustable ring 14, which permits suction device 48 to exert a vacuum force through adjustable ring 14. Catheter 10 can be used with induction coil 20 or alternatively, with induction coil 32.

Catheter 10 is operated in a similar fashion as described above for FIG. 1, at least until adjustable ring 14 is in position within the blood vessel. After adjustable ring 14 is at the desired location within the blood vessel, adjustable ring 14 is expanded at least once, causing the blood vessel to be forcibly dilated. Now the force exerted by suction device 48 through suction tube 50 can remove at least a portion of the deposit or deposits on the wall of the blood vessel. Preferably, adjustable ring 14 is rapidly and repeatedly expanded and contracted in order to more efficiently loosen these deposits from the walls of the blood vessel. This is accomplished by using alternating current through oscillation controller 51, so that adjustable ring 14 can oscillate. In this configuration, the diameter, force and frequency of oscillation can be controlled for maximum efficiency.

One further advantage of this configuration is that the deposits are not left on the wall of the blood vessel and any dislodged debris does not remain in the blood vessel. The likelihood of an embolism occurring can potentially be substantially reduced by removing this debris.

Figure 7A:
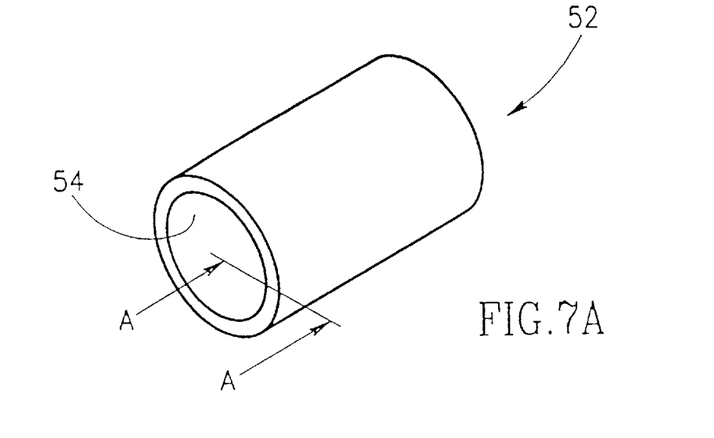
FIGS. 7A, 7B and 7C are views of a stent for use with the present invention.
Figure 7B:
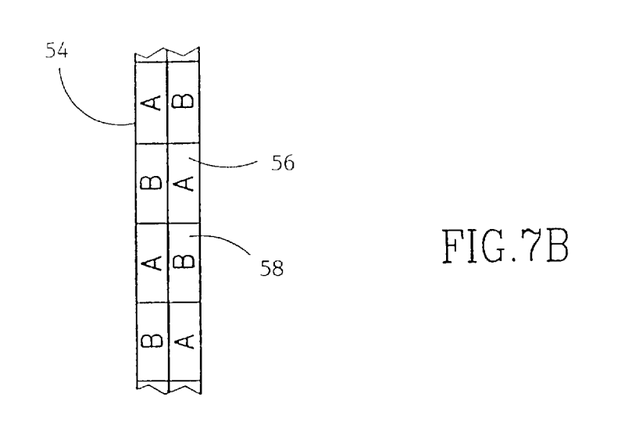
Figure 7C:
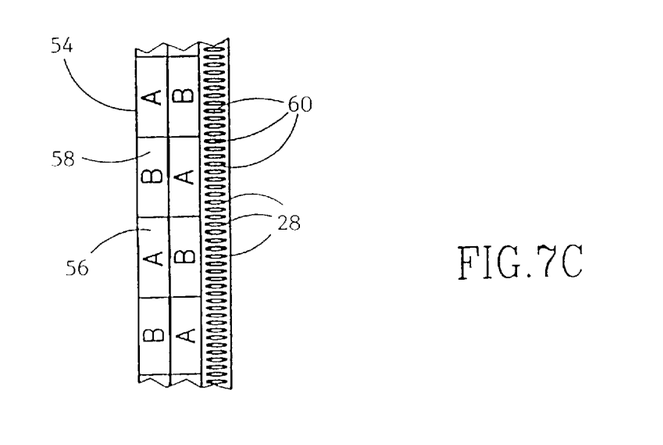

FIGS. 7A, 7B and 7C are views of a stent for repairing a damaged blood vessel wall, which is intended for use with the present invention. Stent 52 alone is shown in FIG. 7A, and reference should also be made to FIGS. 2A, 2B and 6 for the description of operation of stent 52. Stent 52 is made of flexible material and is preferably substantially continuous, such that stent 52 is a single piece of material without a beginning or an end. Stent 52 has a wall 54. Wall 54 can have one of two different configurations, shown in FIGS. 7B and 7C.

FIG. 7B shows a cross-sectional view of stent 52 through line A—A, showing the preferred features of a cell 56 and a cell 58. Each cell 56, of which there is preferably a plurality, contains component "A" of an adhesive. Each cell 58, again of which there is preferably a plurality, contains component "B" of an adhesive. Neither component "A" nor component "B" alone has any adhesive quality. However, when component "A" and component "B" are mixed, the adhesive becomes activated. This mixing takes place when the walls of cells 56 and 58 are ruptured and adjustable ring 14 is oscillated, during the following procedure.

Stent 52 is placed over adjustable ring 14, so that adjustable ring 14 is substantially inside stent 52 (not shown) and stent 52 expands when adjustable ring 14 expands. Next, catheter 10 is placed at the portion of the blood vessel to be repaired, by a substantially similar method to that described for catheter 10 of FIG. 6. Once catheter 10 is in place, adjustable ring 14, and by extension stent 52, is expanded by reversing the direction of current flowing through induction coil 20 or alternatively by allowing current to begin to flow through induction coil 20, so that element 12 now repels adjustable ring 14. The expansion of stent 52 causes cells 56 and 58 to rupture, so that components "A" and "B" can come in contact. As stent 52 is oscillated, or rhythmically expanded and contracted, by the oscillation of adjustable ring 14, components "A" and "B" of the adhesive mix and the adhesive is activated. The adhesive causes stent 52 to become rigid and maintain the extended state of stent 52. After the adhesive is cured, the current can be shut off, or the direction of flow of current reversed, and catheter 10 withdrawn from the subject. Stent 52 remains within the blood vessel because stent 52 maintains the expanded state relative to the diameter of the blood vessel (not shown).

FIG. 7C shows the same cross-sectional view of wall 54, except that the structure of wall 54 has been changed. Now, wall 54 includes at least one, and preferably a plurality of magnetic units 60, so that stent 52 is magnetizable. Each magnetic unit 60 is attached to wall 54, and preferably embedded in wall 54. If there is more than one magnetic unit 60, at least a portion of said magnetic units 60 is arranged with the same pole 28 facing inward towards the interior of stent 52. Each magnetic unit 60 can be any form of material, such as magnetizable metal, which causes stent 52 to be magnetizable including, but not limited to, powder either coated on wall 54 or embedded within wall 54, or both, a chip or a thin section of foil either attached to wall 54 or embedded within wall 54, or both. If powder is used, preferably each magnetic unit 60 is arranged vertically in relation to element 12.

The operation of stent 52 in this embodiment is similar to that described above, except that since stent 52 is directly magnetizable, the magnetic force acts on stent 52 directly, without adjustable ring 14. Furthermore, stent 52 also includes at least one, and preferably a plurality of fibers (not shown), similar to fiber 18. Each fiber attaches stent 52 to element 12, until stent 52 is in place and the adhesive is cured. At that point, each fiber is cut, so that catheter 10 can be withdrawn from the subject, leaving stent 52 behind.

Although the operation of stent 52 has been described using catheter 10 of FIG. 6, it should be understood that the catheters shown in FIGS. 1, 3, 5 or 8–10 can be also be used with stent 52, if the electrical current flowing through the induction coil is alternating current. If alternating current is used, any of these catheters, in combination with stent 52, can be described as a "repair catheter".

Figure 8A:
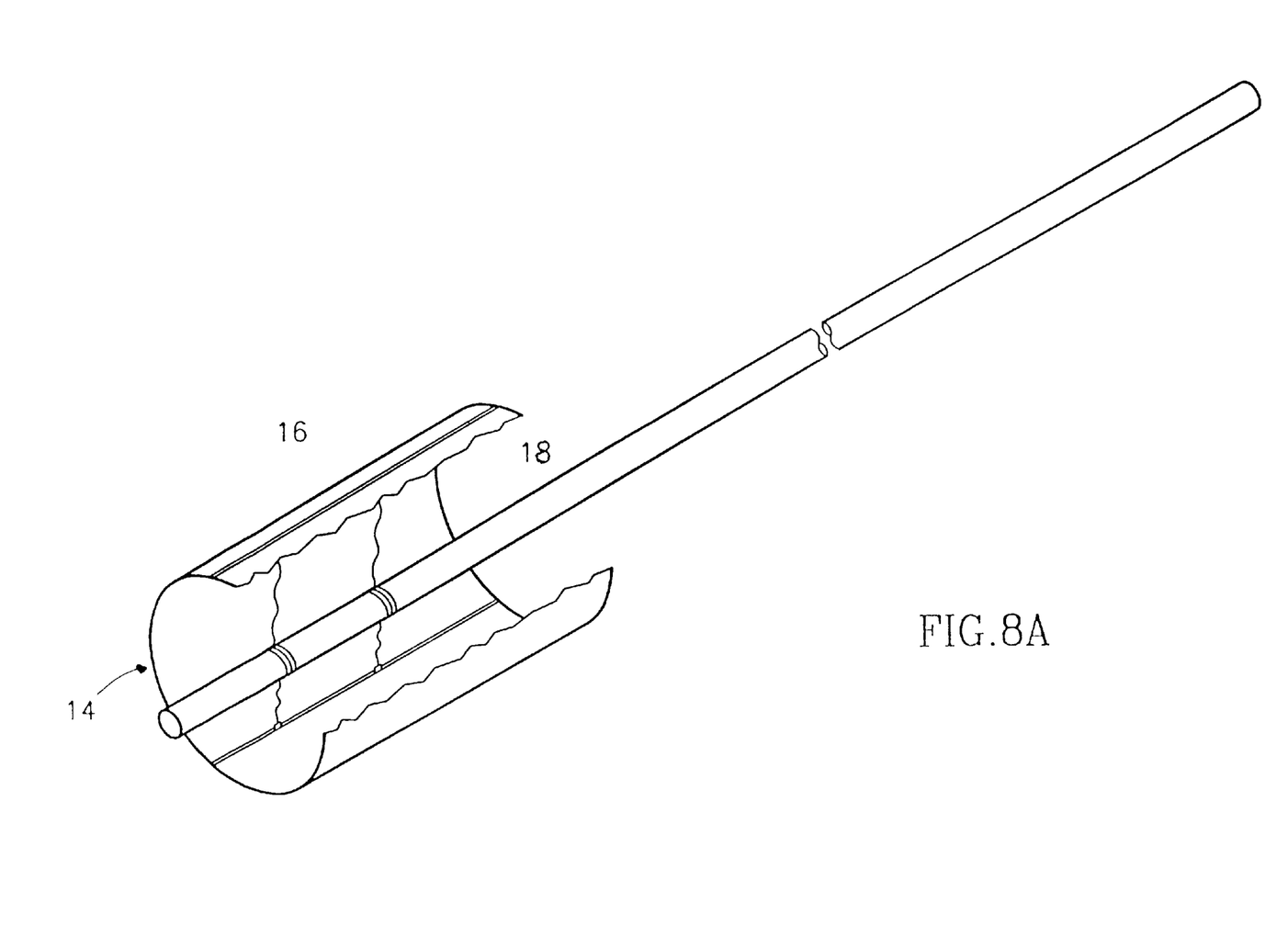
FIGS. 8A and 8B are views of a fifth embodiment of the present invention, in which the diameter of the ring is controlled by an external magnet.
Figure 8B:
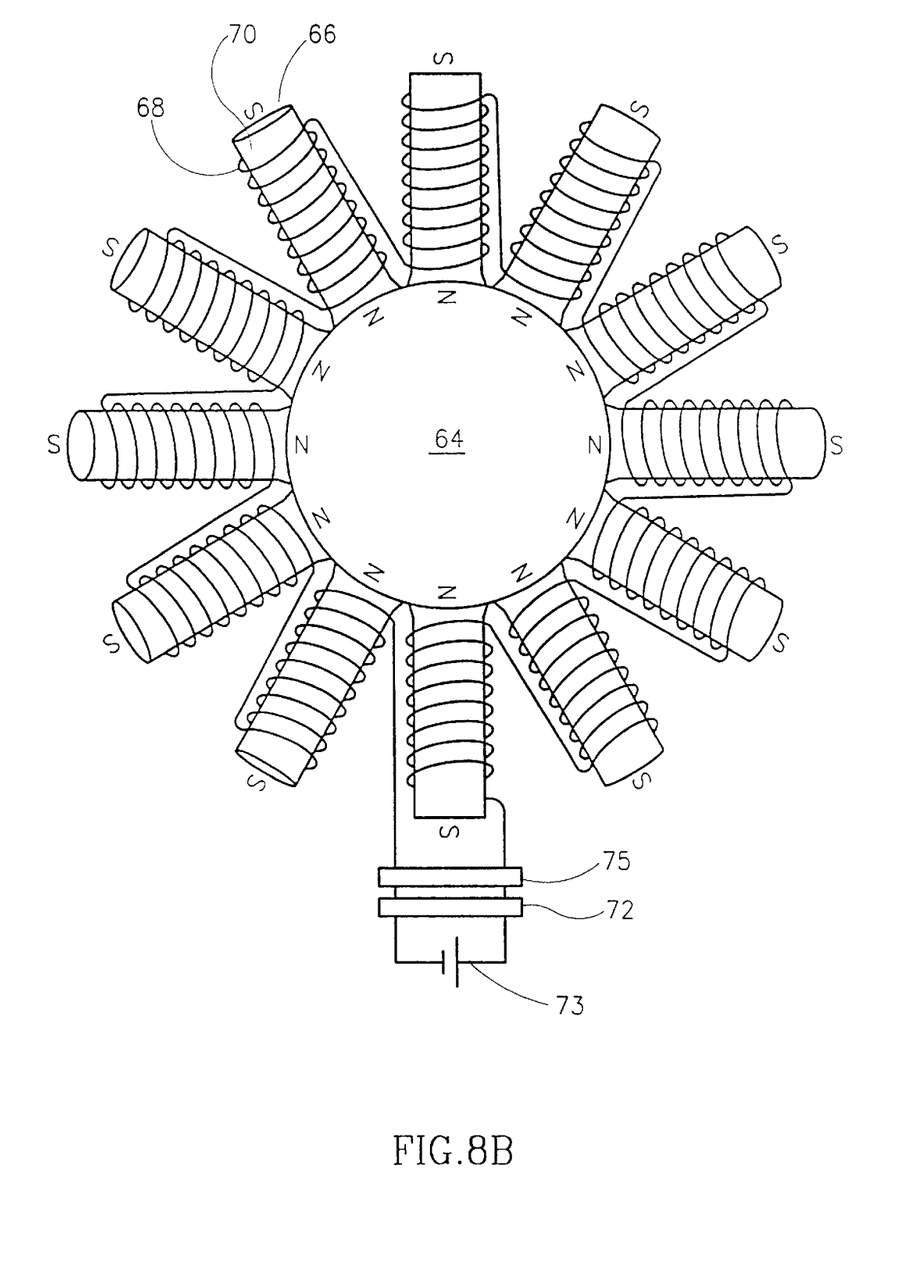

FIGS. 8A and 8B are views of a catheter in which the diameter of the ring is controlled by an external magnet. FIG. 8A shows catheter 10 with an element 62. Element 62 is made of substantially non-magnetizable material. Adjustable ring 14 is substantially similar as shown in FIGS. 1 and 2. However, the magnetic force controlling the diameter of adjustable ring 14 is now supplied outside the body of a subject 64, as shown in FIG. 8B. Subject 64 is shown schematically. At least one, and preferably a plurality of, magnetization units 66 are disposed substantially near subject 64. Each magnetization unit 66 is formed from an induction coil 68 and a conductor 70, preferably with at least one rheostat 72. Induction coil 68 can be a single wire, or alternatively and preferably, induction coil 68 is a plurality of separate wires. In the latter case, each wire of induction coil 68 can be connected together with only one wire directly connected to rheostat 72. Alternatively and preferably, each wire of induction coil 68 can be directly connected to each of a plurality of rheostats 72, so that the flow of electricity, and hence the magnetic force, can be substantially separately regulated for each magnetization unit 66.

Induction coil 68 is wrapped substantially around conductor 70 and is then preferably attached to rheostat 72. Rheostat 72 regulates the flow of electricity from a source of electricity 73 through induction coil 68. A switch (not shown) is preferably used to determine the direction of the flow of electricity. Also preferably, an oscillation controller 75 is also used to permit adjustable ring 14 to be rapidly and repeatedly expanded and contracted in order to more efficiently loosen deposits from the walls of the blood vessel.

However, alternating current must be used with oscillation controller 75. In this configuration, the diameter, force and frequency of oscillation can be controlled for maximum efficiency.

When electricity is permitted to flow through induction coil 68, conductor 70 becomes magnetized. The polarity of conductor 70 depends upon the direction of the flow of electricity through induction coil 68. Electricity flowing through induction coil 68 is preferably alternating current, so that the direction of flow is changeable, although direct current can also be used as described for the catheter of FIGS. 1 and 2.

The operation of catheter 10, as depicted in FIGS. 8A and 8B, is substantially similar to that of the catheter of FIGS. 1 and 2, with one exception. Since the magnetic power is now being supplied outside subject 64 and element 62 is made of substantially non-magnetizable material, the diameter of adjustable ring 14 is now only controlled either by allowing electricity to flow through induction coil 68, or alternatively by changing the direction of electricity flowing through induction coil 68. In the first case, when electricity flows through induction coil 68, adjustable ring 14 expands, and when electricity does not flow through induction coil 68, adjustable ring 14 collapses.

In the second case, when electricity is flowing substantially in one direction, adjustable ring 14 has a first diameter and when electricity is flowing substantially in an opposing direction, adjustable ring 14 has a second diameter. For example, in the first direction, conductor 70 attracts adjustable ring 14, so that adjustable ring 14 expands. Then in the second direction, conductor 70 repels adjustable ring 14, so that adjustable ring 14 contracts. Preferably, a plurality of magnetization units 66 are disposed relatively evenly around subject 64, so that the magnetic force is substantially evenly distributed around subject 64.

Figure 9:
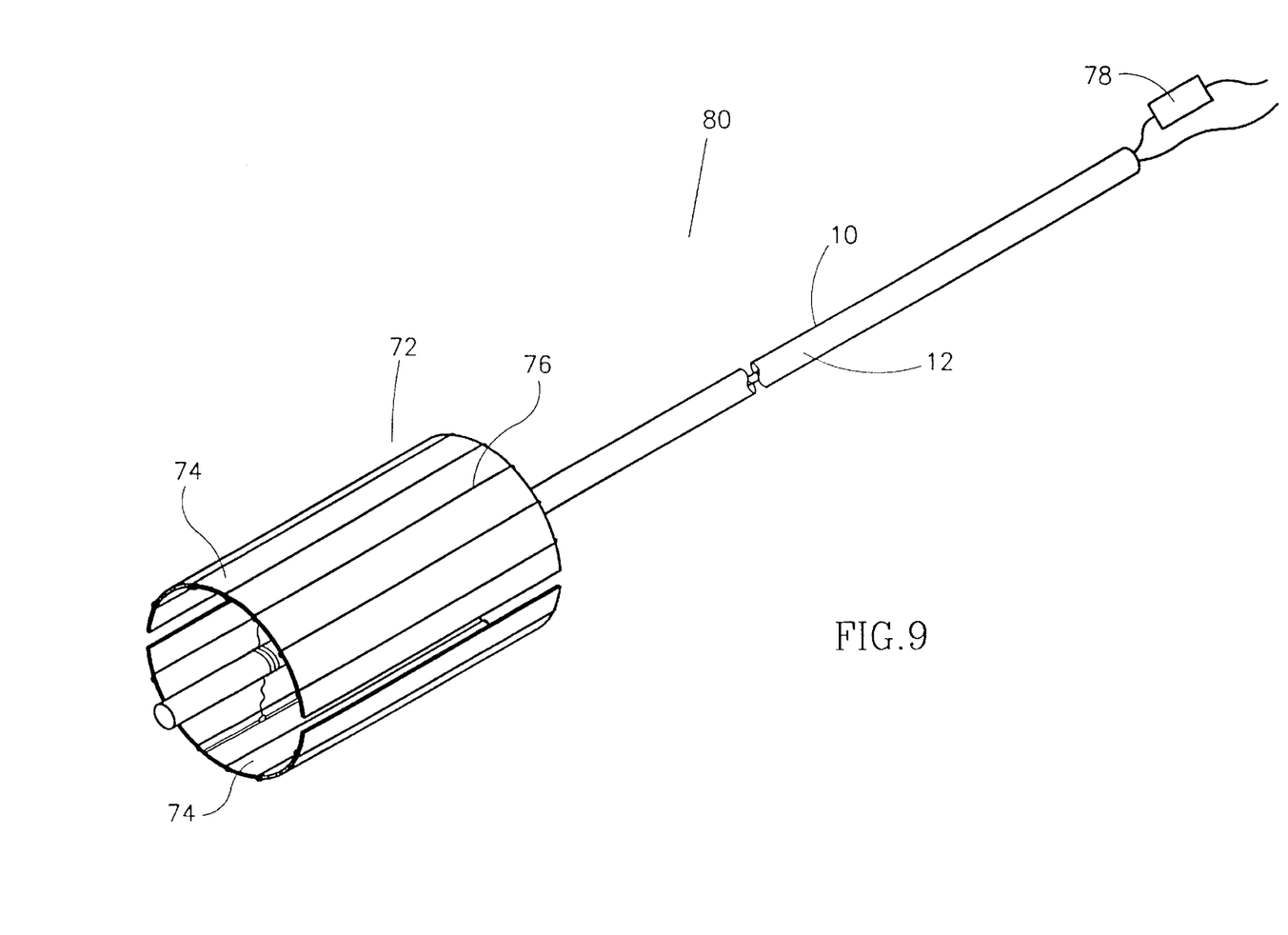
FIG. 9 is a view of a sixth embodiment of the present invention, in which an induction coil is extended along the ring or rings.

FIG. 9 is a view of a catheter in which each induction coil is extended along each adjustable ring. FIG. 9 shows catheter 10 which is substantially similar to the catheter shown in FIGS. 1 and 2, except that the structure of an adjustable ring 72 is different. Preferably, there is a plurality of adjustable rings 72. Each adjustable ring 72 is made of magnetizable metal and is preferably divided into at least two sections 74, and most preferably into more than two sections 74. Each section 74 has an induction coil 76 wrapped substantially around section 74. Induction coil 76 is then preferably attached to rheostat 78. Rheostat 78 regulates the flow of electricity from a source of electricity (not shown) through induction coil 76. A switch (not shown) is preferably used to determine the direction of the flow of electricity. Induction coil 76 and adjustable ring 72 together form a magnetization unit 80, preferably with rheostat 78.

When electricity is permitted to flow through induction coil 76, each adjustable ring 72 becomes magnetized. The polarity of each part 74 of each adjustable ring 72 depends either upon the actual flow of electricity through induction coil 76, or alternatively and preferably, upon the direction of the flow of electricity through induction coil 76. Preferably, electricity flowing through induction coil 76 is alternating current, so that the direction of flow is changeable, although direct current can also be used.

The operation of catheter 10, as depicted in FIG. 9, is substantially similar to that of the catheter of FIGS. 1 and 2, with one exception. The diameter of adjustable ring 72 is now directly controlled either by the actual flow of electricity through induction coil 76, or alternatively and preferably, by the direction of electricity flowing through induction coil 76. In the first case, when electricity flows through induction coil 76, adjustable ring 72 expands, and when electricity does not flow through induction coil 76, adjustable ring 72 collapses.

In the second case, when electricity is flowing substantially in one direction, adjustable ring 72 has a first diameter and when electricity is flowing substantially in an opposing direction, adjustable ring 72 has a second diameter. For example, in the first direction, adjustable ring 72 is repelled from element 12, so that adjustable ring 72 expands. Then in the second direction, adjustable ring 72 is attracted to element 12, so that adjustable ring 72 contracts. One particular advantage of this configuration is that a plurality of adjustable rings 72 can be located along element 12, but controlled individually, so that each adjustable ring 72 can have a different diameter. Furthermore, the horizontal location of each adjustable ring 72 can be adjusted with respect to another adjustable ring 72, by controlling the polarity of rings 72 at one edge so that both adjustable rings 72 repel one another.

Figure 10:
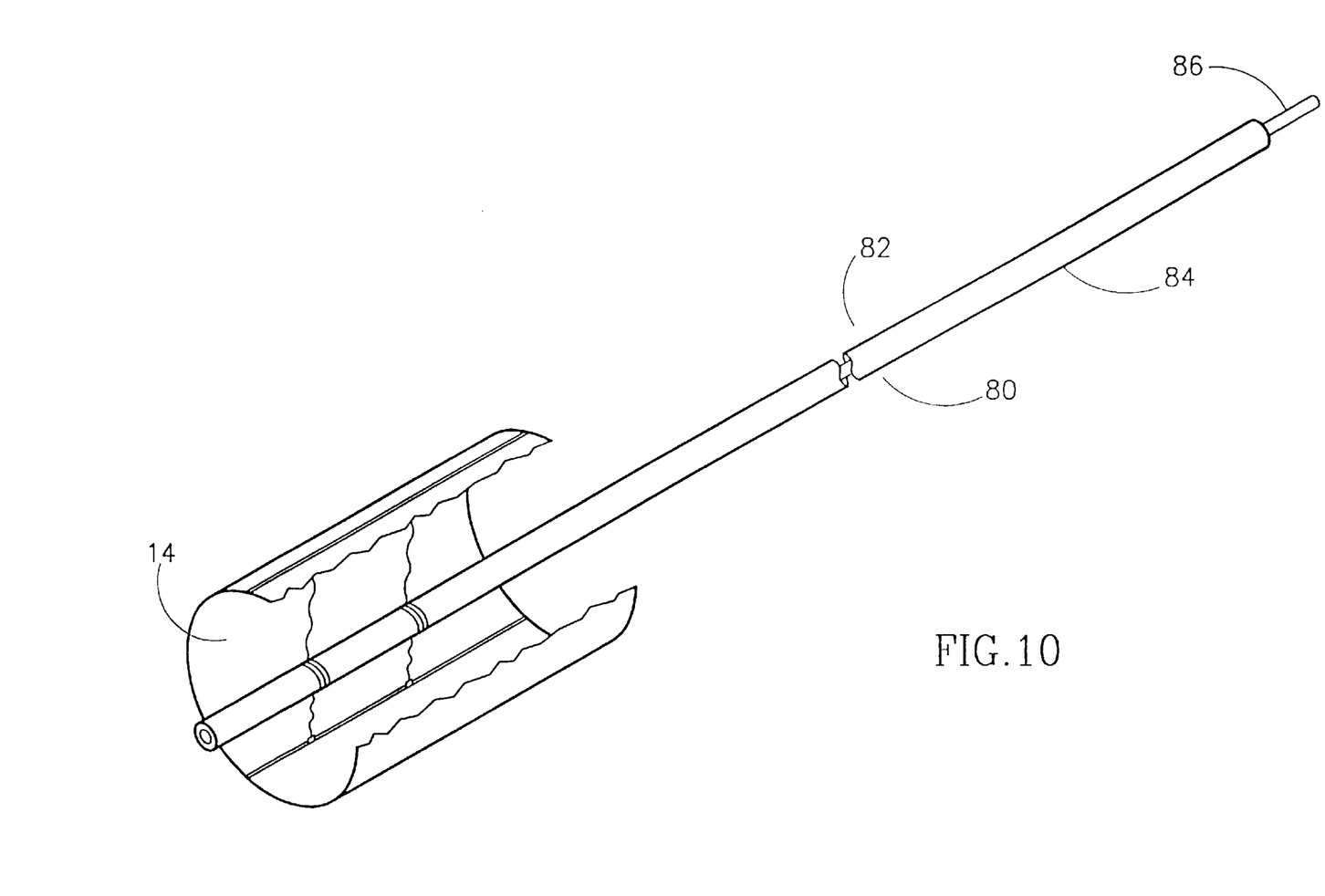
FIG. 10 is a view of a seventh embodiment of the present invention, in which the diameter of the ring is controlled by the insertion and removal of a magnetizable rod.

FIG. 10 shows a catheter in which the magnetic force is controlled by the relative position of an inserted magnetic element. A catheter 80 has an element 82. Element 82 includes a substantially non-magnetizable sheath 84 and a magnetic rod 86. Catheter 80 also has adjustable ring 14. The operation of catheter 80 is as follows. When catheter 80 is inserted into a blood vessel (not shown), adjustable ring 14 has a first diameter. At the appropriate location within the blood vessel, rod 86 is removed, causing adjustable ring 14 to expand to a second, substantially larger diameter (not shown). Alternatively and preferably, rod 86 is not present within sheath 84 when catheter 80 is inserted into the blood vessel. Rod 86 is then inserted into sheath 84 at the appropriate location within the blood vessel, causing adjustable ring 14 to expand. The appropriate behavior of adjustable ring 14 relative to the location of rod 86 depends upon the correct position of the poles of the various magnets, as described above.

While the invention has been described with respect to a limited number of embodiments, it will be appreciated that many variations, modifications and other applications of the invention may be made.

What is claimed is:

1. A catheter, comprising:

(a) an element for transferring a magnetic force;

(b) at least one adjustable ring attached to said element such that at least a portion of said element is substantially within said at least one adjustable ring, said at least one adjustable ring being substantially continuous and said at least one adjustable ring featuring an inner surface, said at least one adjustable ring being alternately dilatable and collapsible in a substantially continuous manner, such that a distance between said inner surface of said at least one adjustable ring and said element is substantially continuously alterable within a range defined between a maximum distance, wherein said at least one adjustable ring is fully dilated, and a minimum distance, wherein said at least one adjustable ring is fully collapsed, and said at least one adjustable ring being magnetizable, such that said distance between said inner surface of said at least one adjustable ring and said element is determined according to an amount of said magnetic force transferred by said element; and (c) a magnetization unit being connected to said element said magnetization unit being located near a portion of said at least one adjustable ring, said magnetization unit determining said amount of said magnetic force transferred by said element.

2. The catheter of claim 1, wherein said magnetization unit includes an induction coil wrapped substantially around said at least one adjustable ring.

3. The catheter of claim 1, wherein said magnetization unit includes an induction coil wrapped substantially around a conductor.

4. A catheter, comprising:

(a) an element for transferring a magnetic force;

(b) at least one adjustable ring attached to said element such that at least a portion of said element is substantially within said at least one adjustable ring, said at least one adjustable ring featuring a plurality of sections, each of said sections featuring an inner surface and an outer surface, each of said plurality of said sections of said at least one adjustable ring being substantially separately alternately dilatable and collapsable in a substantially continuous manner, such that a distance between said inner surface of each of said plurality of said sections of said adjustable ring and said element is substantially continuously alterable within a range defined between a maximum distance, wherein each of said plurality of said sections of said adjustable ring is fully dilated, and a minimum distance, wherein each of said plurality of said sections of said adjustable ring is fully collapsed, each of said plurality of said sections of said at least one adjustable ring being substantially separately magnetizable, such that said distance between said inner surface of each of said plurality of said sections of said adjustable ring and said element is determined according to an amount of said magnetic force transferred by said element; and (c) a magnetization unit located near said element and near a portion of each of said plurality of said sections of said at least one adjustable ring, said magnetization unit determining said amount of said magnetic force transferred by said element.

5. The catheter of claim 1, wherein said element features a magnetic rod, a location of said rod relative to said at least one adjustable ring substantially determining said diameter of said at least one adjustable ring.

6. The catheter of claim 1, further comprising a stent, at least a portion of said at least one adjustable ring being substantially within said stent, said stent having at least a first diameter and at least a second diameter, said stent being magnetizable and said stent containing activatable adhesive, said activatable adhesive being activated when said stent has said second diameter such that said stent becomes substantially rigid.

7. The catheter of claim 1, wherein said at least one adjustable ring is a stent, said stent containing activatable adhesive, said activatable adhesive being activated when said stent has said second diameter such that said stent becomes substantially rigid.

8. A method of catheterizing a biological duct of a subject, the biological duct having a wall, the method comprising the steps of:

(a) providing a catheter featuring:
   (i) an element for transferring a magnetic force;
   (ii) at least one adjustable ring attached to said element such that at least a portion of said element is substantially within said at least one adjustable ring, said at least one adjustable ring being substantially continuous and said at least one adjustable ring featuring an inner surface, said at least one adjustable ring being alternately dilatable and collapsable in a substantially continuous manner, such that a distance between said inner surface of said at least one adjustable ring and said element is substantially continuously alterable within a range defined between a maximum distance, wherein said at least one adjustable ring is fully dilated, and a minimum distance, wherein said at least one adjustable ring is fully collapsed, said at least one adjustable ring being magnetizable, such that said distance between said inner surface of said at least one adjustable ring and said element is determined according to an amount of said magnetic force transferred by said element; and
   (iii) a magnetization unit being located near said element, being located near a portion of said at least one adjustable ring, said magnetization unit determining said amount of said magnetic force transferred by said element;

(b) inserting said catheter into the biological duct of the subject with said at least one adjustable ring of said catheter being substantially fully collapsed such that said at least one adjustable ring substantially does not contact the wall of the biological duct;

(c) causing said at least one adjustable ring to be substantially dilated, such that said at least one adjustable ring is able to contact the wall of the biological duct; and (d) contacting the wall of the biological duct with said at least one adjustable ring.

9. The method of claim 8, wherein the wall of the biological duct is contacted more than once with said at least one adjustable ring.

10. The method of claim 8, further comprising the steps of:

(d) causing said at least one adjustable ring to substantially return to having said first diameter; and (e) withdrawing said catheter from said biological duct.

11. The method of claim 8, wherein said element features a magnetic rod, a location of said rod relative to said at least one adjustable ring substantially determining said diameter of said at least one adjustable ring.

12. A method of catheterizing a biological duct of a subject, the biological duct having a wall, the method comprising the steps of:

(a) providing a catheter featuring:
   (i) an element for transferring a magnetic force;
   (ii) a plurality of adjustable rings attached to said element such that at least a portion of said element is substantially within said plurality of adjustable rings, each of said plurality of adjustable rings having an inner surface, said plurality of adjustable rings being alternately dilatable and collapsable in a substantially continuous manner, such that a distance between said inner surface of each of said plurality of adjustable rings and said element is separately substantially continuously alterable within a range defined between a maximum distance, wherein each of said plurality of adjustable rings is fully dilated, and a minimum distance, wherein each of said plurality of adjustable rings is fully collapsed, said plurality of adjustable rings being magnetizable, such that said distance between said inner surface of each of said plurality of adjustable rings and said element is separately determined according to an amount of said magnetic force transferred by said element; and
   (iii) a magnetization unit located near said element and located near a portion of each of said plurality of adjustable rings, said magnetization unit determining said amount of said magnetic force transferred by said element;

(b) inserting said catheter into the biological duct of the subject with said plurality of adjustable rings of said catheter being substantially fully collapsed such that said plurality of adjustable rings substantially do not contact the wall of the biological duct;

(c) causing at least one of said plurality of adjustable rings to be substantially dilated, such that said at least one of said plurality of adjustable rings is able to contact the wall of the biological duct; and (d) contacting the wall of the biological duct with said at least one of said plurality of adjustable rings.

* * * * *